US012765933B2

(12) United States Patent
Nonnenmann et al.

(10) Patent No.: US 12,765,933 B2
(45) Date of Patent: Oct. 20, 2026

(54) MEDICAL IMPACT INSTRUMENT

(71) Applicant: Aesculap AG, Tuttlingen (DE)

(72) Inventors: Martin Nonnenmann, Wurmlingen (DE); Mattea Buggle, Schwaigern (DE)

(73) Assignee: Aesculap AG, Tuttlingen (DE)

( * ) Notice: Subject to any disclaimer, the term of this patent is extended or adjusted under 35 U.S.C. 154(b) by 129 days.

(21) Appl. No.: 18/358,296

(22) Filed: Jul. 25, 2023

(65) Prior Publication Data

US 2024/0032978 A1 Feb. 1, 2024

(30) Foreign Application Priority Data

Jul. 28, 2022 (DE) ..................... 10 2022 118 986.4

(51) Int. Cl.
*A61B 17/92* (2006.01)

(52) U.S. Cl.
CPC ........ *A61B 17/92* (2013.01); *A61B 2017/922* (2013.01)

(58) Field of Classification Search
CPC .................................... A61B 17/92–2017/928
See application file for complete search history.

(56) References Cited

U.S. PATENT DOCUMENTS 843,655 A * 2/1907 Adell et al. .............. B25D 5/00 30/367
1,572,046 A * 2/1926 Seiler ....................... B25D 5/02 81/463
2,337,971 A * 12/1943 Oscar ....................... A61C 3/16 433/151
2,421,354 A * 5/1947 Reiter ...................... A61C 3/08 606/100
3,177,952 A * 4/1965 West ........................ B25D 5/00 173/124
5,398,861 A * 3/1995 Green .................... A61B 17/92 227/19
5,735,855 A * 4/1998 Bradley ............. A61B 17/1604 606/86 R
5,741,268 A * 4/1998 Schutz ............... A61B 17/0642 606/104
5,788,701 A 8/1998 McCue
(Continued)

FOREIGN PATENT DOCUMENTS

EP 0780090 A1 6/1997
EP 1308143 A2 5/2003
JP 2016022234 A 2/2016

*Primary Examiner* — Zade Coley
(74) *Attorney, Agent, or Firm* — Christopher A. Rothe; CM Law

(57) ABSTRACT

A medical impact instrument, in particular in the form of an impact hammer, includes a shaft defining a shaft longitudinal direction, a proximal end and a distal end. An impact body is arranged on the shaft and defines a longitudinal axis. The impact body is movable in an impact position on the shaft between a distal stop defining a distal stop position of the impact body and a proximal stop defining a proximal stop position of the impact body for transmitting an impact pulse to the distal end of the shaft in the distal or proximal direction. The impact instrument includes a fixing device for temporarily fixing the impact body to the shaft in at least one, in particular arbitrary, fixing position between the distal stop position and the proximal stop position.

22 Claims, 9 Drawing Sheets

(56) References Cited

U.S. PATENT DOCUMENTS

| | | | | | |
|---|---|---|---|---|---|
| 5,827,290 | A * | 10/1998 | Bradley | A61B 17/1604 | 606/85 |
| 5,904,284 | A * | 5/1999 | Lin | B25C 1/082 | 227/8 |
| 5,921,456 | A * | 7/1999 | Kirsch | A61B 17/92 | 173/124 |
| 6,010,508 | A * | 1/2000 | Bradley | A61B 17/92 | 606/86 R |
| 6,273,893 | B1 * | 8/2001 | McAllen, III | A61B 17/8872 | 606/104 |
| 7,708,739 | B2 * | 5/2010 | Kilburn | A61F 2/4607 | 606/86 R |
| 8,201,481 | B2 * | 6/2012 | Williams | B25C 7/00 | 227/113 |
| 8,435,241 | B2 * | 5/2013 | Correia | A61B 17/92 | 606/86 R |
| 8,486,084 | B2 * | 7/2013 | Huene | A61B 17/92 | 606/100 |
| 9,827,027 | B2 * | 11/2017 | Black | A61B 17/8872 | |
| 10,052,145 | B2 | 8/2018 | Capek et al. | | |
| 11,534,214 | B2 * | 12/2022 | Black | A61B 17/8033 | |
| 2003/0083668 | A1 | 5/2003 | Rogers et al. | | |
| 2006/0178673 | A1 * | 8/2006 | Curran | A61B 17/92 | 606/100 |
| 2010/0076438 | A1 * | 3/2010 | Correia | A61B 17/92 | 606/87 |
| 2010/0331851 | A1 * | 12/2010 | Huene | A61B 17/92 | 606/100 |
| 2016/0138669 | A1 * | 5/2016 | Yang | B25B 27/02 | 254/133 R |
| 2018/0177536 | A1 | 6/2018 | Divincenzo et al. | | |
| 2021/0378840 | A1 | 12/2021 | Mueller et al. | | |
| 2023/0139058 | A1 * | 5/2023 | Terziotti | A61B 17/92 | 606/100 |

* cited by examiner

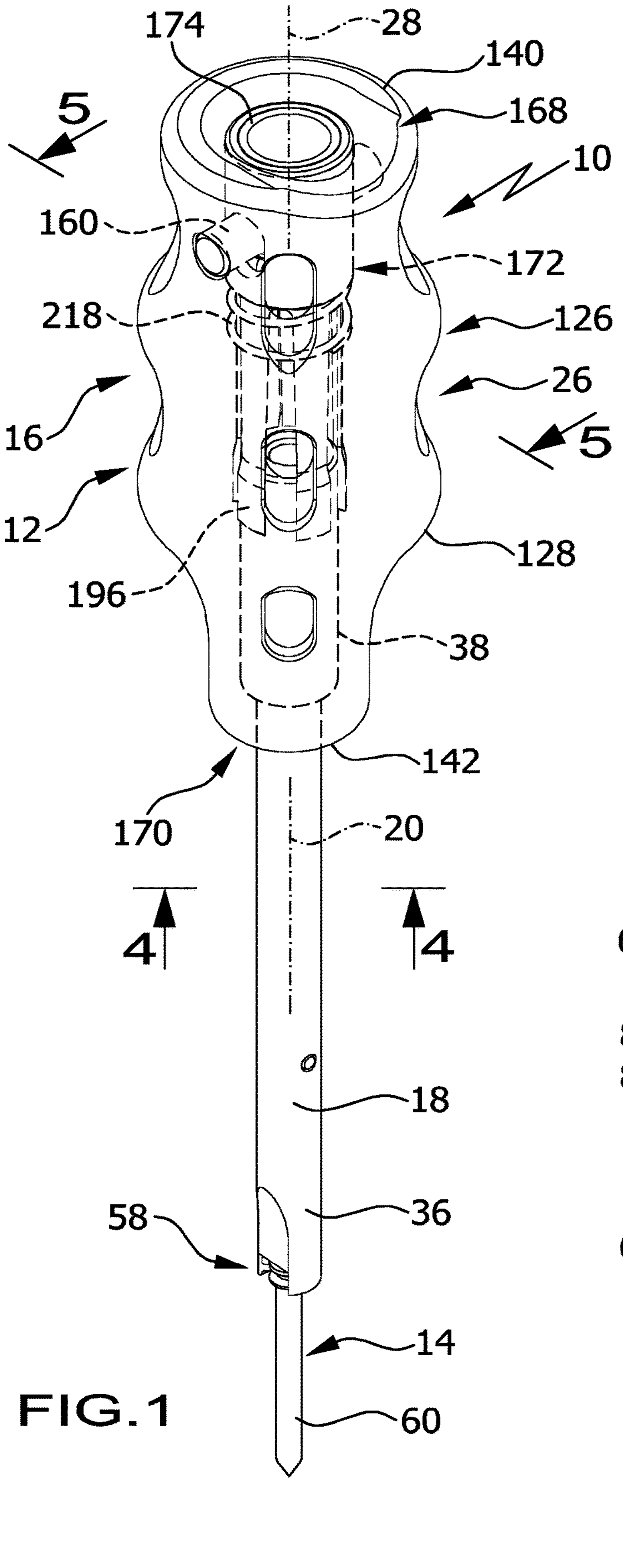
FIG.1
FIG.2
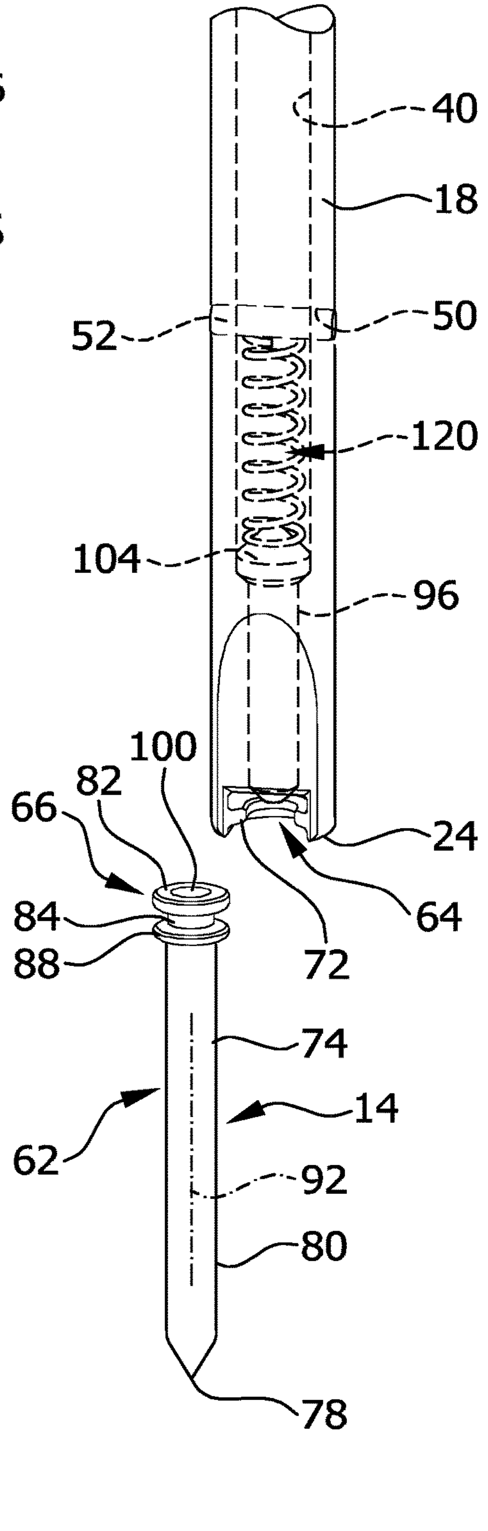

MEDICAL IMPACT INSTRUMENT

CROSS-REFERENCE TO RELATED APPLICATIONS

The present disclosure claims priority to German Patent Application No. 10 2022 118 986.4, filed Jul. 28, 2022, the content of which is incorporated by reference herein in its entirety and for all purposes.

FIELD

The present disclosure relates to medical impact instruments generally, and more specifically to a medical impact instrument, in particular in the form of an impact hammer, comprising a shaft defining a shaft longitudinal direction and a proximal and a distal end, and comprising an impact body arranged on the shaft and defining a longitudinal axis, wherein the impact body in an impact position on the shaft is movable, in particular displaceable, between a distal stop defining a distal stop position of the impact body and a proximal stop defining a proximal stop position for transmitting an impact pulse to the distal end of the shaft in the distal or proximal direction.

BACKGROUND

Medical impact instruments of the kind described at the outset are known, for example, in the form of impact hammers, also referred to as so-called "slap hammers", in different variants. Distal ends of the impact instruments can be coupled, e.g., to implants in order to, for example, strike them into or out of a bone by transmitting impact pulses. Such an impact instrument may optionally also be coupled, in particular with its distal end, to a medical object. Due to the mobility of the impact body and the shaft relative to one another, it is necessary for achieving such a coupling to handle the impact instrument with two hands, namely holding the shaft and the impact body each with one hand. However, this is disadvantageous, in particular, in a medical operation in an operating room, because an operation time should always be kept as short as possible and also a simple handling of instruments used here is desirable.

SUMMARY

In a first aspect of the present disclosure, a medical impact instrument, in particular in the form of an impact hammer, comprises a shaft defining a shaft longitudinal direction as well as a proximal and a distal end, and comprising an impact body arranged on the shaft and defining a longitudinal axis. The impact body in an impact position on the shaft is movable, in particular displaceable, between a distal stop defining a distal stop position of the impact body and a proximal stop defining a proximal stop position of the impact body for transmitting an impact pulse to the distal end of the shaft in the distal or proximal direction. The impact instrument comprises a fixing device for temporarily fixing the impact body to the shaft in at least one, in particular an arbitrary, fixing position between the distal stop position and the proximal stop position.

BRIEF DESCRIPTION OF THE DRAWING FIGURES

The foregoing summary and the following description may be better understood in conjunction with the drawing figures.

FIG. 1 shows a schematic, partially broken total view of an embodiment of a medical system comprising a medical impact instrument with a medical object coupled thereto;

FIG. 2 shows a perspective, partially broken view of a distal end of the impact instrument from FIG. 1 with a medical object separated therefrom;

Figure 8:
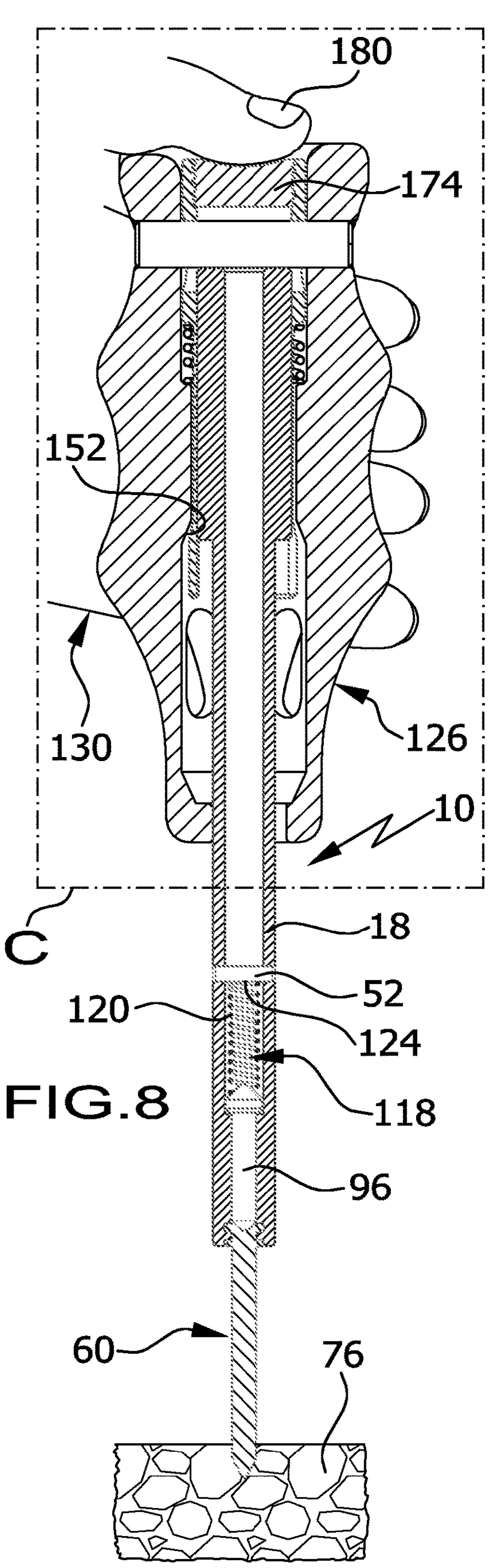
FIG. 8 shows a view similar to FIG. 5, but upon transferring the impact instrument from the locking position into the release position.
Figure 13:
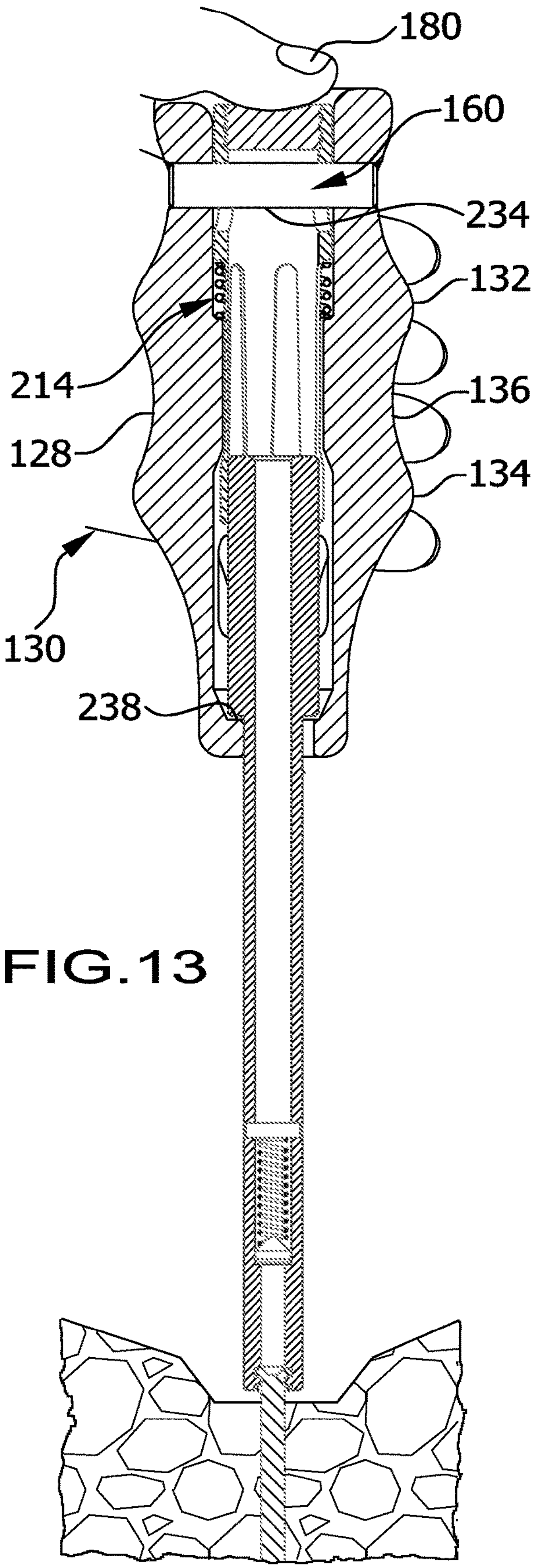
Figure 14:
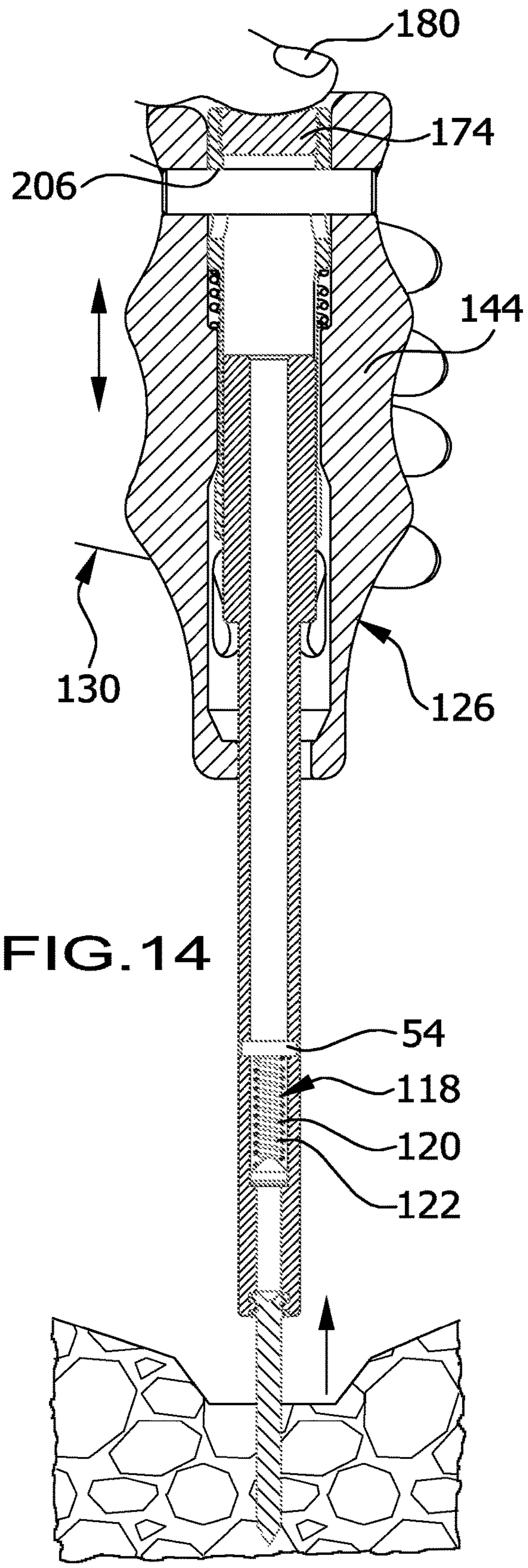

FIG. 13 shows a view similar to FIG. 8, i.e. with the impact instrument in the impact position and the impact body in the proximal stop position upon exerting an impact pulse in the proximal direction for extracting the medical object from a bone; and FIG. 14 shows a view similar to FIG. 8, wherein the impact instrument adopts the impact position before exerting an impact pulse in the proximal direction.

DETAILED DESCRIPTION

Although the present disclosure is illustrated and described herein with reference to specific embodiments, the present disclosure is not intended to be limited to the details shown. Rather, various modifications may be made in the details within the scope and range of equivalents and without departing from the present disclosure.

The present disclosure relates to a medical impact instrument, in particular in the form of an impact hammer, comprising a shaft defining a shaft longitudinal direction as well as a proximal and a distal end, and comprising an impact body arranged on the shaft and defining a longitudinal axis, wherein the impact body in an impact position on the shaft is movable, in particular displaceable, between a distal stop defining a distal stop position of the impact body and a proximal stop defining a proximal stop position of the impact body for transmitting an impact pulse to the distal end of the shaft in the distal or proximal direction, wherein the impact instrument comprises a fixing device for temporarily fixing the impact body to the shaft in at least one, in particular an arbitrary, fixing position between the distal stop position and the proximal stop position.

A medical impact instrument with such a fixing device enables a user, in particular, to fix or lock the impact body to the shaft in one or more, in particular in a plurality, and also an arbitrary fixing position. Fixing in this sense is to be understood to mean that the impact body and the shaft are immovable relative to one another in the fixing position. One could also say that the shaft is immovably held to the impact body in the fixing position. This fixing of the impact body to the shaft simplifies the handling of the medical impact instrument. When the impact body is fixed to the shaft, a user can handle the impact instrument with only one hand without the help of a second hand and, for example, can couple it to a medical object, for example a fastening element in the form of a pin. In other words, the fixing device enables, in particular, a simple one-hand operation of the medical impact instrument.

The impact body is favorably configured in the form of a handle. This makes it possible, in particular, to grip the medical impact instrument at the impact body with one hand and to then handle it with one hand, in particular in order to couple it to a medical object. To this end, the medical impact instrument is preferably transferred with the fixing device into a fixing position.

For optimal handling, it is advantageous if the handle has an ergonomically formed outer contour for holding same with one hand.

It is favorable if the impact body in a basic position is fixed relative to the shaft and adopts the at least one fixing position. A user can thus grip the impact instrument, in particular, at the impact body with one hand, the impact body then remaining immovable relative to a distal end of the impact instrument. The impact instrument can thus be coupled to a medical object in a simple manner.

It is advantageous if the fixing device is configured to fix the impact body to the shaft in the proximal stop position and/or in the distal stop position. The fixing device is thus suited not only to fix the impact body to the shaft in at least one or an arbitrary number of fixing positions between the distal and the proximal stop position, but also in the extreme positions of the impact body, namely the proximal stop position and the distal stop position.

In accordance with a further preferred embodiment, provision may be made that the fixing device is transferable from a fixing position, in which the impact body is fixed to the shaft in any one of the fixing positions, into the impact position, in which the impact body and the shaft are movable relative to one another, and vice versa. This configuration enables a user, in particular, to transfer the impact body from the fixing position into the impact position, in order to exert impact pulses with the impact body of the impact instrument on the distal end thereof, namely optionally in the distal or in the proximal direction. In particular, the fixing device may be configured in such a way that an actuation by a user is actively necessary to not only transfer the fixing device from the fixing position into the impact position, but also to hold it in said impact position.

The fixing device favorably comprises a restoring device for automatically holding the fixing device in the fixing position. This configuration has the advantage, in particular, that the impact body is held on the shaft in one of the possible fixing positions without a user have to actuate the fixing device in any way. Thus, in particular, an unintentional and undesired movement of the impact body relative to the shaft can be prevented.

The fixing device can advantageously be brought from the locking position into the impact position against the action of the restoring device. A user therefore must exert a force in order to actuate the fixing device, in particular in such a way that it is transferred from the locking position into the impact position.

The restoring device can be formed in a simple manner if it comprises at least one restoring element.

The restoring device can be made in a simple and cost-effective manner if the at least one restoring element is configured in the form of a rubber-elastic or spring-elastic element.

The at least one restoring element is preferably configured in the form of a compression or tension spring. This makes it possible, in particular, to transfer the fixing device from the fixing position into the impact position by exerting a compressive or tensile force counter to the action of the at least one restoring element.

In accordance with a further preferred embodiment, provision may be made that the fixing device comprises at least one fixing element for being brought into force-locking and/or positive-locking engagement both with the shaft and with the impact body in the at least one fixing position. This configuration makes it possible, for example, to configure the fixing element to be movable, namely both relative to the shaft and relative to the impact body in the impact position. In the fixing position, the at least one fixing element can then, in particular, block a relative movement between the impact body and the shaft, for example by engaging both with the impact body and with the shaft in a force-locking and/or positive-locking manner.

The restoring device can be arranged and a compact impact instrument can be formed in a simple manner if the at least one restoring element is supported on a fixing element support face of the at least one fixing element on the one hand and on an impact body support face of the impact body on the other hand. Such a configuration makes it possible, in particular, to arrange the at least one restoring element inside the impact body in a protected manner. Inside in this sense means within an envelope surface that is defined by the impact body and preferably has a constant tangent. Furthermore, it is thus also possible, in particular, to move the fixing element relative to the impact body against the action of the at least one restoring element. For example, the impact body can be gripped with one hand and the at least one fixing element can be moved relative to the impact body, for example displaced in the distal direction, by actuating with one finger.

It is advantageous if the fixing element support face is configured pointing in the distal direction and if the impact body support face is configured pointing in the proximal direction. Both the fixing element support face and the impact body support face may be configured, e.g., as annular faces. This makes it possible, in particular, to use the stated support faces in cooperation with a restoring element in the form of a coil or helical spring.

It is favorable if the at least one fixing element is movable relative to the impact body for transferring the fixing device from the fixing position into the impact position. In particular, the at least one fixing element may be arranged or formed so as to be displaceable relative to the impact body. For example, the at least one fixing element may be movably, in particular displaceably, mounted on the impact body. This configuration enables, in particular, a simple one-hand operation by a user, who holds the impact body with their hand and displaces the at least one fixing element with a finger, for example their thumb, in order to transfer the fixing device from the locking position into the impact position.

The impact instrument can be configured in a simple and compact manner if the at least one fixing element is of sleeve-shaped configuration.

It is favorable if the at least one fixing element is movable relative to the impact body in the distal direction for transferring the fixing device from the locking position into the impact position. This configuration makes it possible, in particular, for a user to push the at least one fixing element in the distal direction with their thumb while they are holding the impact body with the same hand.

A proximal end of the at least one fixing element in the locking position preferably does not or substantially does not protrude beyond a proximal end of the impact body. This makes it possible, in particular, to use the impact instrument in the manner of a chisel and, for example, to act on the proximal end of the impact body with a hammer without thereby moving the fixing element in the distal direction, which would thereby transfer the impact body fixed relative to the shaft into the impact position.

In particular, in order to minimize a risk of injury, for example the risk of damage to a glove of a user, it is advantageous if the at least one fixing element is closed on the proximal side. In particular, the fixing element on the proximal side may be shaped to be concavely or convexly curved pointing in the proximal direction.

It is favorable if the impact body comprises a fixing element stop device with a distal and a proximal fixing element stop for delimiting a movement of the at least one fixing element in the distal and proximal direction. A configuration of that kind enables a simple handling of the impact instrument. A user can thus, for example, simply push the at least one fixing element against the distal fixing element stop for transferring the impact instrument from the fixing position into the impact position. The proximal fixing element stop delimits the movement of the at least one fixing element in the proximal direction. In particular, the restoring device can push the at least one fixing element against the proximal fixing element stop in the basic position.

It is advantageous if the at least one fixing element comprises a fixing element perforation, which extends transversely, in particular perpendicularly to the longitudinal axis and if the fixing element stop device passes through the fixing element perforation. This enables, in particular, a simple configuration of the impact instrument. The fixing element perforation may comprise, for example, rim or edge portions that point in the distal and in the proximal direction and that in cooperation with the fixing element stop device define the distal and proximal fixing element stops.

The distal fixing element stop is preferably arranged or formed on the proximal side relative to the proximal fixing element stop. This enables a particularly compact structure of the medical impact instrument.

It is favorable if the at least one fixing element is configured in the form of a clamping element and comprises at least one clamping arm extending in the longitudinal direction, and if a free end of the at least one clamping arm is configured to be movable, in particular pivotable, in the direction toward and away from the longitudinal axis of the shaft. Fixing elements of that kind make it possible, in particular in a simple manner, to achieve a clamping relative to the shaft. For example, this can be achieved by pushing the free end of the at least one clamping arm in the direction toward the longitudinal axis of the shaft.

The impact body preferably comprises a recess surrounding the shaft for accommodating the at least one clamping element. The recess makes it possible, in particular, for the free end of the at least one clamping element to be pivoted away from the shaft in order to release the shaft. In other words, a clamping between the at least one fixing element and the shaft can thus be released.

It is advantageous if the recess is delimited at least in sections by a clamping face pointing in the direction toward the longitudinal axis, which clamping face in the locking position cooperates with the at least one clamping element for preventing a movement of the free end of the at least one clamping element away from the longitudinal axis or for clampingly holding the at least one clamping element in the direction toward the longitudinal axis. For example, the free end of the at least one clamping element can slide on the clamping face for transferring the impact instrument from the impact position into the locking position.

The clamping face favorably expands conically in the distal direction and forms a sliding face. A relative movement between the free end of the at least one clamping element and the impact body can thus be enabled or prevented or blocked in a simple manner.

It is advantageous if formed on the free end of the clamping element is a sliding face, which points away from the longitudinal axis, is inclined relative to the longitudinal axis, and cooperates with the clamping face of the impact body. The sliding face on the free end of the clamping element, in particular in cooperation with the clamping face of the impact body, can help to prevent an unintentional jamming and thus blocking of the fixing device.

A first angle of inclination defined between the clamping face and the longitudinal axis is preferably greater than a second angle of inclination defined between the sliding face and the longitudinal axis. The different first and second angles of inclination make it possible, in particular, to prevent a self-locking between the fixing element and the impact body when using the impact instrument. Thus, they ensure, in particular, a reliable functioning of the impact instrument, in particular of its fixing device.

In accordance with a preferred embodiment, provision may be made that the impact body has a longitudinal perforation extending coaxially to the shaft longitudinal direction and that the shaft is accommodated at least partially in the longitudinal perforation. For example, the proximal shaft portion can be completely accommodated in the longitudinal perforation, independent of a relative position of the impact body and the shaft. The longitudinal perforation can also simplify an assembly of the impact instrument. It can thus optionally be easily and quickly disassembled for cleaning.

It is advantageous if the shaft comprises a distal shaft portion and a proximal shaft portion, if the proximal shaft portion is accommodated in the longitudinal perforation, and if the distal shaft portion projects out of the longitudinal perforation on the distal side. Such a configuration makes it possible, in particular, to design the impact instrument in such a way that the impact body, independently of a relative position to the shaft, also always defines the proximal end of the impact instrument with its proximal end.

It is advantageous if an inner face of the at least one fixing element pointing toward the longitudinal direction forms a guide face for the proximal shaft portion. This makes it possible, in particular, to move the at least one fixing element in a defined manner relative to the shaft, namely, for example, relative to the proximal shaft portion.

Furthermore, it may be advantageous if the longitudinal perforation of the impact body commencing from its proximal end forms a guide face pointing in the direction toward the longitudinal axis for the at least one fixing element. Due to this guide face, the at least one fixing element can be moved relative to the impact body in a defined manner. In particular, the guide face may be configured in such a way that a jamming of the fixing element relative to the impact body in the region of the guide face is not possible.

It is favorable if the proximal shaft portion comprises the distal stop with a first stop face that acts in the proximal direction, and if the impact body comprises a first impact body stop face that acts in the distal direction, which in the distal stop position interacts with the first stop face. For example, the impact instrument can be made in a simple manner by a proximal end face of the proximal shaft portion defining the first stop face.

The impact instrument can be formed in a simple and compact manner if the impact body comprises a stop element, which defines the first impact body stop face. In particular, the stop element can delimit not only a movement of the shaft relative to the impact body, but also a movement of the at least one fixing element relative to the impact body.

It is advantageous if the stop element defines a stop element longitudinal axis and if the stop element longitudinal axis extends transversely, in particular perpendicularly, to the shaft longitudinal direction. The stop element can thus be arranged or held, for example, transversely on the impact body.

The stop element can be easily configured in the form of a stop pin inserted into a transverse bore on the impact body.

A distance of the stop element from the proximal end of the impact body is preferably smaller than a distance from the distal end of the impact body. This enables a maximum stroke of the shaft, in particular of its proximal shaft portion, relative to the impact body, in particular in the longitudinal perforation formed on the impact body.

The fixing element stop device favorably comprises the stop element. It is thus possible, in particular, for the fixing element stop device to take on a plurality of functions. A compact structure of the impact instrument can be achieved in this way.

It is advantageous if the at least one restoring element is arranged or formed on the distal side of the stop element. It may thus be configured, e.g., in the form of a pressure element, which is compressed in the distal direction by moving the at least one fixing element.

Furthermore, it is favorable if the proximal shaft portion comprises the proximal stop with a second stop face acting in the distal direction and if the impact body comprises a second impact body stop face acting in the proximal direction, which in the proximal stop position cooperates with the second stop face. This configuration enables, in particular, a simple delimitation of a movement of the impact body relative to the shaft in the proximal direction.

A compact structure of the impact instrument can be achieved, in particular, if the distal delimiting wall comprises the second impact body stop face.

It is advantageous if a first distance between the first stop face and the second stop face is smaller than a second distance between the first impact body stop face and the second impact body stop face. In particular, a movement of the shaft relative to the impact body is made possible by this configuration. The difference between the two distances determines a maximum stroke of the impact body relative to the shaft.

The at least one restoring element is favorably arranged or formed surrounding the at least one fixing element. It is thus possible, in particular, to arrange the restoring element on the impact instrument in a protected manner, so that its functioning can be permanently ensured.

The impact body favorably comprises at least one flush opening. The flush opening can, in particular, establish a fluid connection between an environment of the impact body and the longitudinal perforation thereof. The impact instrument can thus be cleaned in a simple and secure manner, in particular without disassembling it.

The at least one flush opening is preferably formed in the region of a peripheral wall of the impact body surrounding the longitudinal axis or in the region of a distal delimiting wall of the impact body. It is therefore possible, in particular, to provide two or more flush openings, namely, for example, both in the region of the peripheral wall and in the region of the distal delimiting wall. Thus, in particular, a cleaning fluid is able to flow through the impact instrument for cleaning in order to securely remove contaminants.

It is advantageous if the longitudinal perforation passes through the distal delimiting wall and in the region of the distal delimiting wall forms a guide face for the distal shaft portion. In this way, in particular, a movement of the impact body relative to the shaft can be guided in a simple and defined manner. In particular, the guide face may be formed circumferentially. It may also be interrupted by at least one flush opening. In particular, the guide face may be of hollow-cylindrical configuration or comprise hollow-cylindrical surface portions.

In accordance with a further preferred embodiment, provision may be made that the impact instrument comprises a coupling device for temporarily coupling to a medical object. As explained at the outset, the impact instrument can thus be coupled, e.g., to a fastening element in order to strike it out of a bone in which it was anchored. For this purpose, impact pulses are transmitted from the impact body to the shaft in the impact position, namely when the impact body cooperates with the proximal stop that defines the proximal stop position.

It is advantageous if the medical object is configured in the form of a medical implant. For example, it may be configured in the form of a medical fastening element or in the form of an implant component of a joint implant. The medical impact instrument can thus be used, in particular, for anchoring or releasing the medical objects to or from a bone. Furthermore, a medical system comprising a medical impact instrument and at least one medical object can thus be defined.

It is favorable if the coupling device comprises a first coupling element, which is configured to be brought into force-locking and/or positive-locking engagement with a corresponding second coupling element comprised by the medical object in a coupling position. The coupling device enables, in particular, a simple and secure connection of the impact instrument to a medical object in the coupling position.

The coupling device can be formed in a simple manner if the first coupling element is configured in the form of a coupling projection or a coupling receptacle. The second coupling element can then be configured corresponding to the first coupling element in the form of a coupling receptacle or a coupling projection.

It is favorable if the coupling device comprises a securing device for securing a medical object to the medical impact instrument in the coupling position in a force-locking and/or positive-locking manner. The impact instrument can be coupled to the medical instrument by means of the coupling device. Independently thereof, the securing device serves to secure the medical object to the impact instrument in the coupling position, for example against unintentional release. Thus, in particular, a reliable handling of the impact instrument can be achieved. Thus, in particular, a risk of the medical object coupled to the impact instrument falling off the impact instrument in an undesirable manner can be significantly reduced.

It is favorable if the securing device is able to be brought from a release position, in which the medical impact instrument and the medical object are able to be brought into engagement in an engagement direction, into a securing position, in which a movement of the medical impact instrument and the medical object relative to one another in or opposite to the engagement direction is blocked. In other words, the securing device and the coupling device operate in linearly independent directions so that, in particular, an unintentional release of the medical object from the impact instrument is possible only after overcoming a release force for deactivating the securing device.

The impact instrument can be made in a simple manner if the engagement direction extends transversely, in particular perpendicularly, to the shaft longitudinal direction. Thus, as already indicated, linearly independent movements can be achieved in order to secure the medical object to the shaft in the coupling position in a defined manner.

It is advantageous if the securing device comprises a securing member, which is in force-locking and/or positive-locking engagement with a securing element of the medical object in the securing position. The securing member can thus secure the medical object to the shaft in the coupling position, in particular in a defined manner, namely when the securing member adopts not the release position, but rather the securing position.

The securing member is favorably movably, in particular displaceably, mounted on the shaft. A simple securing mechanism for the medical object on the impact instrument can thus be achieved.

It is advantageous if the securing device comprises a securing member stop against which the securing member strikes in the securing position. The securing member stop may serve the purpose, in particular, that the securing member is not able to fall off the shaft in the distal direction in an undesirable manner. The securing member stop therefore serves to delimit a movement of the securing member, in particular in the distal direction.

The securing device can be made in a simple manner if the securing member stop comprises a stop face pointing in the proximal direction. A movement of the securing member in the distal direction can thus be blocked when it cooperates with the stop face of the securing member stop.

It is favorable if the securing member comprises a securing member shaft and a securing member head arranged or formed thereon on the proximal side and if the securing member head is configured to cooperate with the securing member stop. In other words, the securing member head also forms a stop or a stop face, which cooperates with the securing member stop in order to, in particular, delimit a movement of the securing member in the distal direction.

It is advantageous if the securing member head comprises a securing member head stop face, which points in the distal direction and cooperates with the stop face of the securing member stop. In particular, a movement of the securing member in the distal direction can thus be delimited in a simple manner.

The movement of the securing member in the distal direction can be delimited in a simple manner if the stop face is configured in the form of an annular face. The securing member head stop face may also be configured in the form of an annular face.

Furthermore, provision may be made that the securing member comprises a distal securing member end that can be brought into engagement with the medical object, and that the distal securing member end is rounded pointing in the distal direction. Thus, in particular, a risk of injury when using the impact instrument can be avoided. In addition, the rounded securing member end can prevent jamming with a projection or a recess on the medical object, for example when coupling or decoupling same.

The securing device favorably comprises a biasing device for automatically transferring the securing device from the release position into the securing position. As a result of the biasing device, it is thus achieved, in particular, that the securing device always adopts the securing position, without additional external forces. For example, by means of the biasing device, the securing device can be configured in the form of a latching or snapping connecting device, which enables a simple, in particular toolless coupling of the impact instrument to the medical object.

It is advantageous if the biasing device is configured to hold the securing member under bias in the securing position. The medical object can thus, in particular, be secured to the impact instrument in the coupling position with the securing device in a simple and secure manner.

The biasing device can be configured in a simple manner if it comprises at least one biasing element.

The at least one biasing element is favorably configured in the form of a rubber-elastic or spring-elastic element. These can be produced in a simple and cost-effective manner, for example from materials that are sterilizable with hot steam.

Depending on the configuration of the securing device, it may be advantageous if the biasing element is configured in the form of a compression or tension spring.

The at least one biasing element is preferably supported on the securing member on the one hand and on a support face pointing in the distal direction on the other hand. Such a configuration is advantageous, in particular, when using a biasing element in the form of a pressure element, i.e. a compression spring, for example.

It is favorable if the securing device comprises a support element arranged on the shaft and if the support element comprises the support face. The support element together with the support face thus forms, in particular, a stop for the biasing element and thus, in particular, also a stop for a movement of the securing member in the proximal direction.

The support element can be configured in a simple manner if it defines a support element longitudinal axis and if the support element longitudinal axis extends transversely, in particular perpendicularly, to the shaft longitudinal direction.

The impact instrument can be formed in a simple and cost-effective manner if the support element is configured in the form of a pin inserted into a transverse bore on the shaft. The pin may, for example, be screwed into the transverse bore and/or be materially bonded to the shaft, for example by adhesion, soldering, or welding.

An embodiment of a medical system denoted as a whole with the reference numeral 10 is schematically depicted in FIG. 1. The medical system 10 comprises a medical impact instrument 12 and a medical object 14, which are described in detail in the following.

The embodiment of the medical impact instrument 12 depicted in the Figures is configured in the form of an impact hammer 16. Said impact hammer 16 comprises a shaft 18, which defines a shaft longitudinal direction 20 as well as a proximal end 22 and a distal end 24. Arranged on the shaft 18 is an impact body 26, which defines a longitudinal axis 28.

The impact body 26 is moveable, namely displaceable, on the shaft 18 in an impact position, namely between a distal stop position, which is defined by a distal stop 30, and a proximal stop position, which is defined by a proximal stop 32. This arrangement enables the transmission of an impact pulse to the distal end 24 of the shaft 18 in the distal and in the proximal direction.

The impact instrument 12 comprises a fixing device, which is denoted as a whole with the reference numeral 34. It serves to temporarily fix the impact body 26 to the shaft 18 in an arbitrary fixing position between the distal stop position and the proximal stop position.

The shaft 18 comprises a distal shaft portion 36 and a proximal shaft portion 38.

The shaft 18 is passed through by a longitudinal channel 40 from the proximal end 22 to the distal end 24.

An outer diameter of the proximal shaft portion 38 is greater than an outer diameter of the distal shaft portion 36, such that an annular face 42 pointing in the distal direction is formed in the transition between the proximal shaft portion 38 and the distal shaft portion 36.

The proximal shaft portion 38 comprises the distal stop 30 with a first stop face 44, which acts in the proximal direction and forms a proximal end face 46 of the shaft 18. The first stop face 44 is of annular configuration.

The proximal shaft portion 38 also comprises the proximal stop 32 with a second stop face 48, which points in the distal direction and is formed by the annular face 42.

Formed on the distal shaft portion 36 is a transverse bore 50, into which a support element 52 in the form of a cylindrical pin 54 is inserted. The support element 52 defines a support element longitudinal axis 56, which extends transversely, namely perpendicularly in the embodiment depicted in the Figures, to the shaft longitudinal direction 20. A distance of the transverse bore from the distal end 24 corresponds to about a distance of the annular face 42 from the proximal end 22 of the shaft 18.

On the impact instrument 12, namely on its shaft 18, a coupling device 58 is provided for temporarily coupling to the medical object 14.

In the Figures, the medical object 14 as one possible embodiment is configured in the form of a medical implant 60. Furthermore, the medical implant 60 is depicted as an example in the Figures in the form of a medical fastening element 62. Alternatively, the medical object 14 may also be configured in the form of an implant component of a joint implant. Here, different kinds of shafts, that are insertable into bone cavities, or also joint cups of ball joints are conceivable.

The coupling device 58 comprises a first coupling element 64, which is formed near the distal end 24 of the shaft 18. The first coupling element 64 is configured to be brought into force-locking and/or positive-locking engagement with a corresponding second coupling element 66 in a coupling position. In the case of the medical system 10 depicted in the Figures, the medical object 14 comprises the second coupling element 66.

The first coupling element 64 comprises a coupling receptacle 68 in the form of an annular groove 70, which concentrically surrounds the longitudinal axis 28 and is open pointing toward said longitudinal axis 28. The annular groove 70 is adjoined on the distal side by an annular flange that projects in the direction toward the longitudinal axis 28.

The medical fastening element 62 is configured in the form of a bone pin 74, which has on its distal end a tip 78 for driving into a bone 76 of a patient.

The medical fastening element 62 comprises a cylindrical shaft 80, which extends from the tip 78 up to a proximal end of the medical fastening element 62 on which the second coupling element 66 in the form of a head 82 is formed. Formed on the head 82 is an annular groove 84, which points away from the longitudinal axis 28 and into which the annular flange 72 engages in the coupling position, as is depicted as an example in FIG. 7.

The distal shaft portion 36 is provided with a chamfer 86 on one side commencing from the distal end 24, such that the coupling receptacle 68 is laterally open. This enables a lateral insertion of the head 82 into the coupling receptacle 68.

Due to the configuration of the annular groove 84, a second annular flange 88 is formed, which delimits the head 82 on the distal side.

The head 82 and the first coupling element 64 are configured in such a way that they are able to be brought into engagement with one another in an engagement direction 90. The engagement direction 90 extends transversely, namely perpendicularly in the embodiment depicted in the Figures, to the shaft longitudinal direction 20. For coupling the impact instrument 12 and the medical object 14, a shaft axis 92 defined by the shaft 80 of the bone pin 74 and the longitudinal axis 28 must be oriented in parallel to one another.

FIG. 1 shows the coupling position of the impact instrument 12 and the medical object 14. The bone pin 74 before being coupled to the first coupling element 64 of the coupling device 58 is schematically depicted in FIG. 2.

The coupling device 58 comprises a securing device 94 for securing the medical object 14 to the medical impact instrument 12 in the coupling position in a force-locking and/or positive-locking manner.

The securing device 94 is configured in such a way that it is able to be brought from a release position, in which the medical impact instrument 12 and the medical object 14 are able to be brought into engagement in the engagement direction 90, into a securing position, in which a movement of the medical impact instrument 12 and the medical object 14 relative to one another in or opposite to the engagement direction 90 is blocked.

The securing device 94 comprises a securing member 96, which is in force-locking and/or positive-locking engagement with a securing element 98 of the medical object 14 in the securing position. The securing element 98 is configured in the form of a depression 100 on the head 82. The depression 100 is open pointing in the proximal direction.

The securing member 94 comprises a cylindrical securing member shaft 102 with a securing member head 104 arranged or formed thereon on the proximal side. The securing member head 104 forms a proximal end of the securing member 96.

The securing member head 104 defines an outer diameter, which is greater than the outer diameter of the securing member shaft 102. A securing member head stop face 106 that points in the distal direction is thereby formed in the transition region between the securing member head 104 and the securing member shaft 102.

Figure 3:
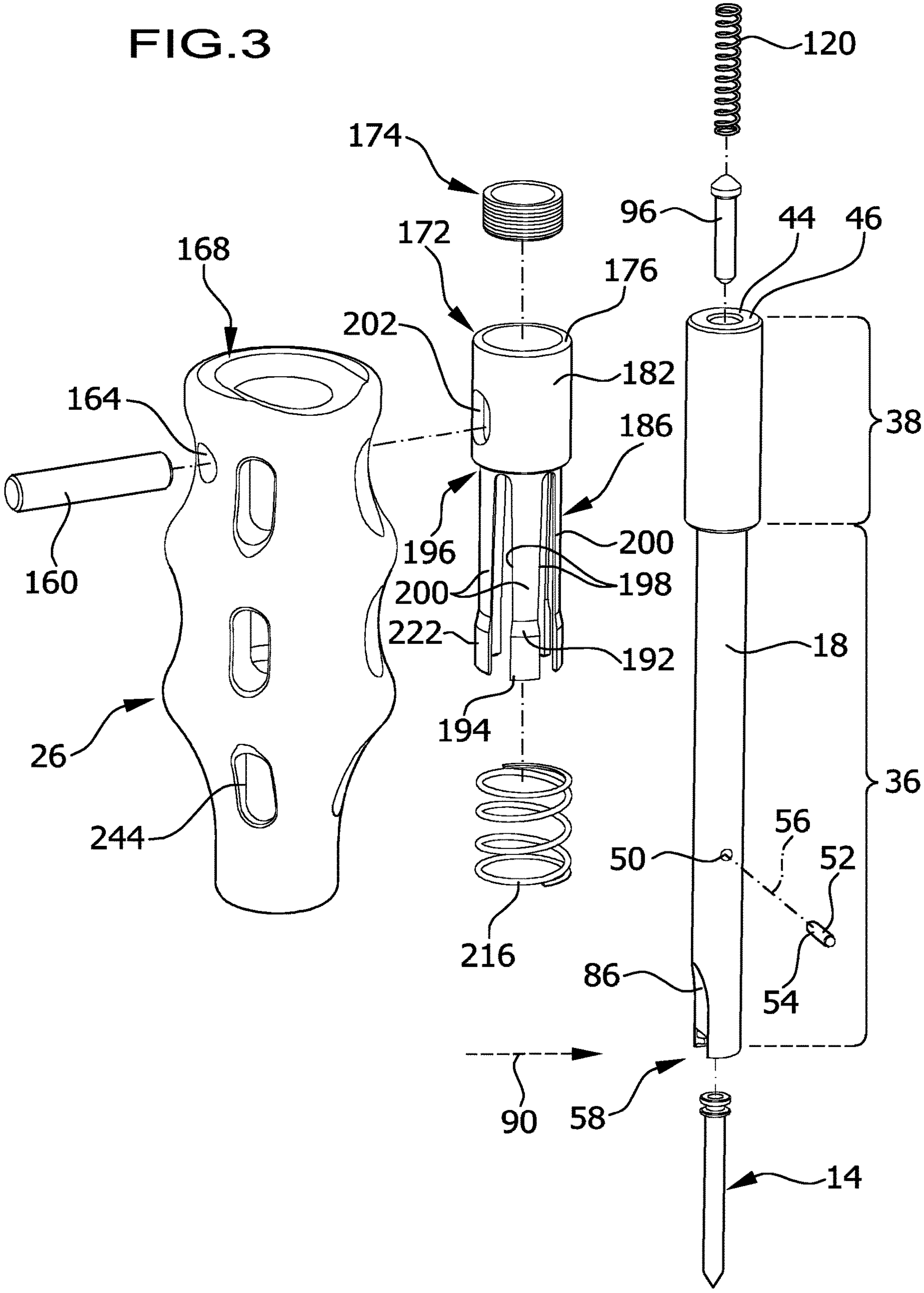
FIG. 3 shows a perspective exploded depiction of the arrangement from FIG. 1.
Figure 4:
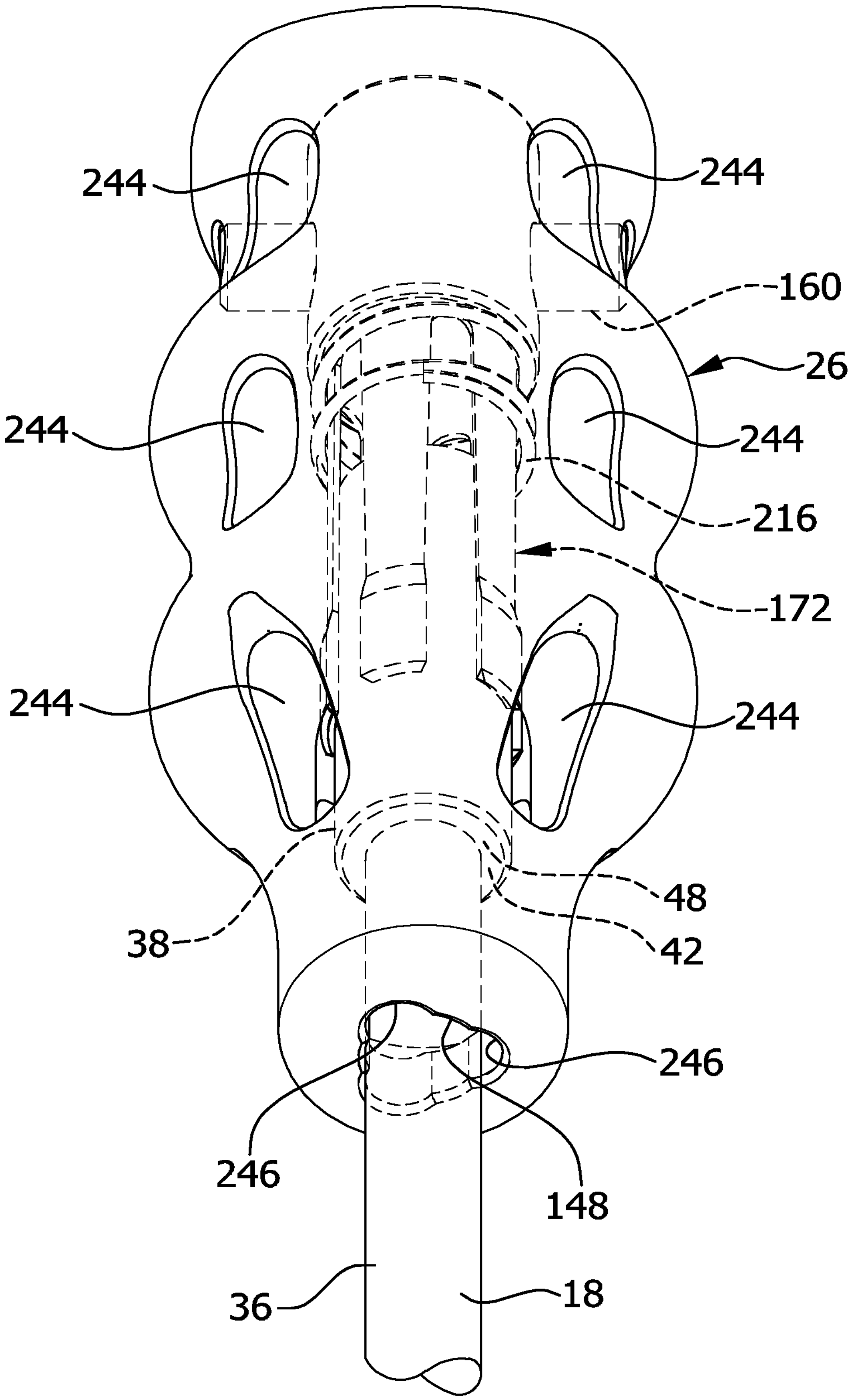
FIG. 4 shows a perspective view of a proximal end region of the impact instrument from FIG. 1.
Figure 5:
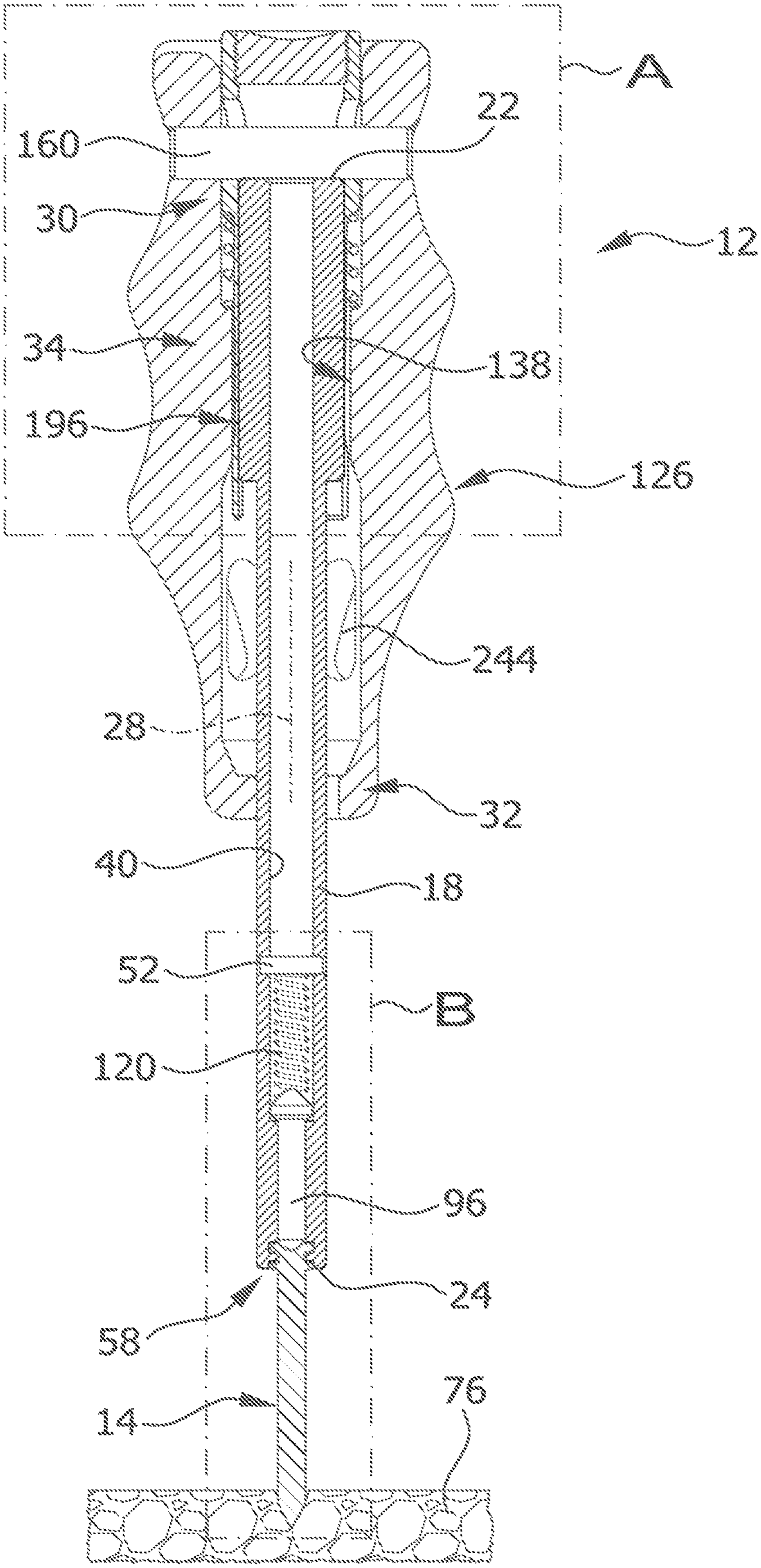
FIG. 5 shows a section view along line 5-5 in FIG. 1.
Figure 7:
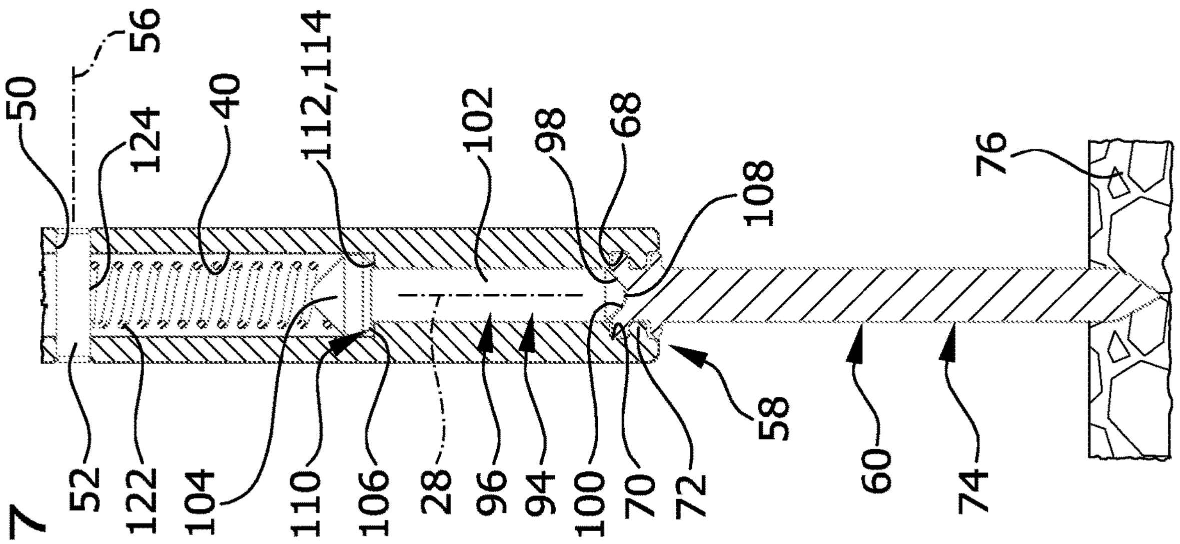
FIG. 7 shows an enlarged view of the region B in FIG. 5.

A distal securing member end 108 of the securing member 96 is able to be brought into engagement with the medical object 14, namely with the depression 100. The distal securing member end 108 is rounded pointing in the distal direction. A contour of the distal securing member end 18 and the depression 100 correspond to one another, as is schematically depicted in FIG. 7. FIG. 7 shows the securing position.

Between the distal end 24 of the shaft 18 and the transverse bore 50, an inner diameter of the longitudinal channel 40 expands in one step, such that a securing member stop 110 is formed. The securing member stop 110 comprises a stop face 112, which points in the proximal direction and is of annular configuration. An inner diameter of the longitudinal channel 40 on the distal side of the stop face 112 corresponds to an outer diameter of the securing member shaft 102. The securing member 96 is thus held in the longitudinal channel of the shaft 18 in a displaceably guided manner.

The securing member stop 110 of the securing device 94 delimits a movement of the securing member 96 on the shaft 18 in the distal direction. The securing member 96 strikes with its securing member head 104 in the securing position against the securing member stop 110. The securing member head 104 and the securing member stop 110 are thus configured to cooperate with one another. In the securing position, the securing member head stop face 106 abuts against the stop face 112. The stop face 112 is configured in the form of an annular face 114.

The securing device 94 comprises a biasing device 116 for automatically transferring the securing device 94 from the release position into the securing position. In the embodiment depicted in the Figures, the biasing device 116 holds the securing member 96 under bias in the securing position. For this purpose, the biasing device 116 comprises a biasing element 118. The biasing element 118 is configured as a spring-elastic element 120. In alternative embodiments, the biasing element may be configured in the form of a rubber-elastic element.

The biasing element 118 is configured in the form of a compression spring 122.

Furthermore, the biasing element 118 is supported distally on the securing member 96, namely on its conically tapering securing member head 104 pointing in the proximal direction on the one hand and on a support face 124 acting in the distal direction on the other hand. The securing device 94 also comprises the support element 52 arranged on the shaft 18. The support element 52, in turn, comprises the support face 124. This is an outer face of the support element 52 pointing in the distal direction 52.

The described securing device 94 is configured in such a way that the compression spring 122 holds the securing member 96 under bias in the distal direction.

When the head 82 of the bone pin 74 is introduced into the coupling receptacle 68 commencing from the separating position schematically depicted in FIG. 2, in which the medical object 14 and the medical impact instrument 12 are completely out of engagement, in the engagement direction 90, i.e. transversely to the longitudinal axis 28, the rounded distal securing member end 108 slides on the head 82 and is moved by the latter against the action of the biasing element 118 in the proximal direction. When the head 82 is completely accommodated by the first coupling element 64, the compression spring 122 can move the securing member 96 back in the distal direction, such that the distal securing member end 108 is able to dip into the depression 100 and thus secure the bone pin 74 against undesired decoupling from the medical impact instrument 12. The described securing device 94 is thus configured in the manner of a latching or snapping connecting device.

Figure 9:
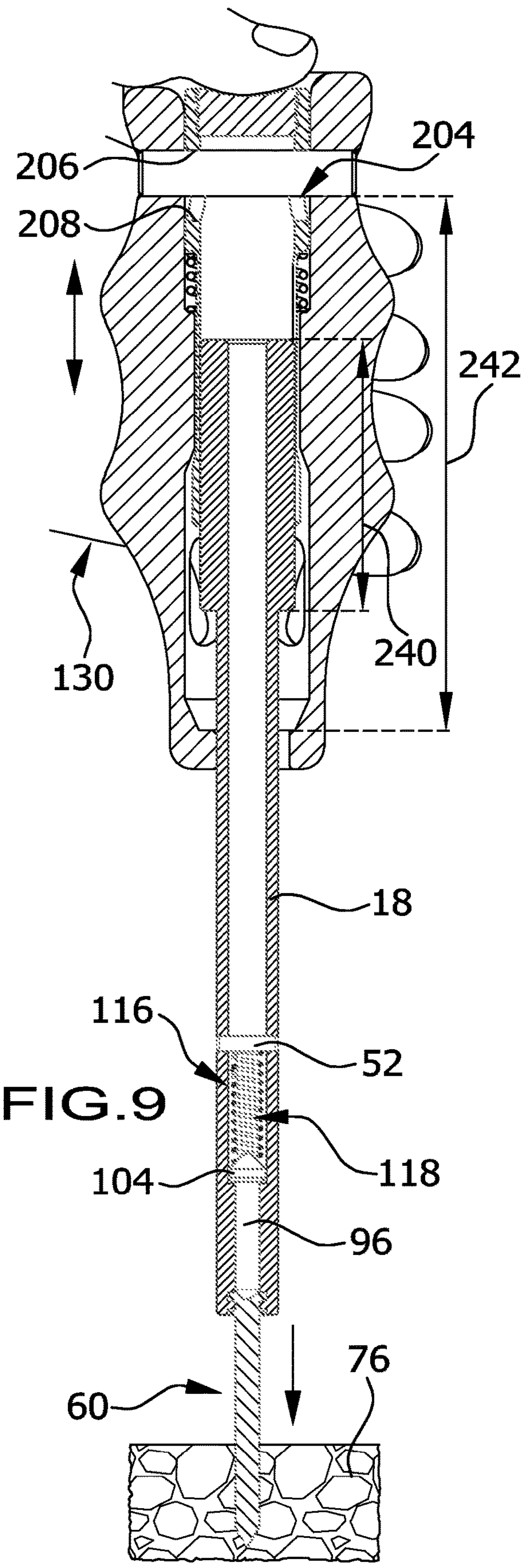
FIG. 9 shows a schematic depiction similar to FIG. 8, but upon moving the impact body relative to the shaft in the distal or proximal direction.
Figure 10:
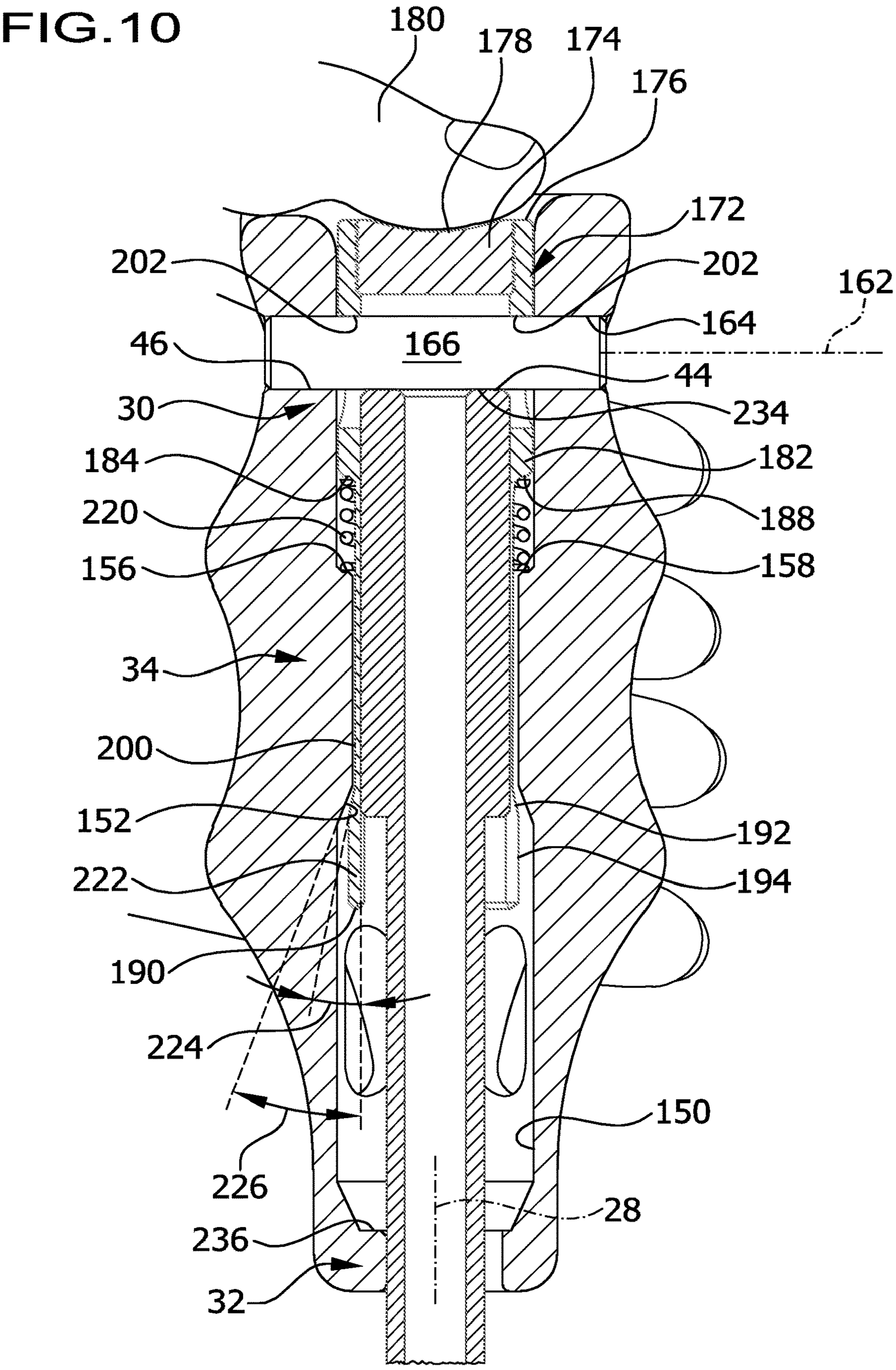
FIG. 10 shows an enlarged view of the region C in FIG. 8.
Figure 11:
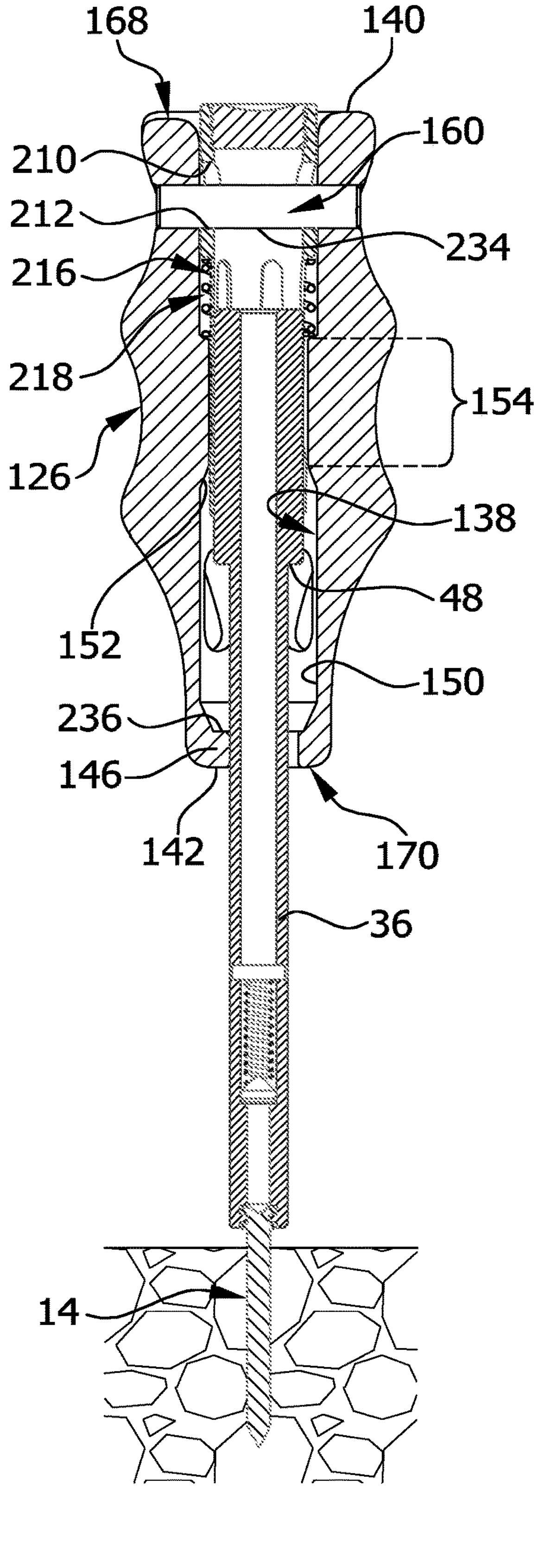
FIG. 11 shows a view similar to FIG. 5, wherein the impact body is clampingly held to the shaft in an arbitrary fixing position between the distal and the proximal stop position.
Figure 12:
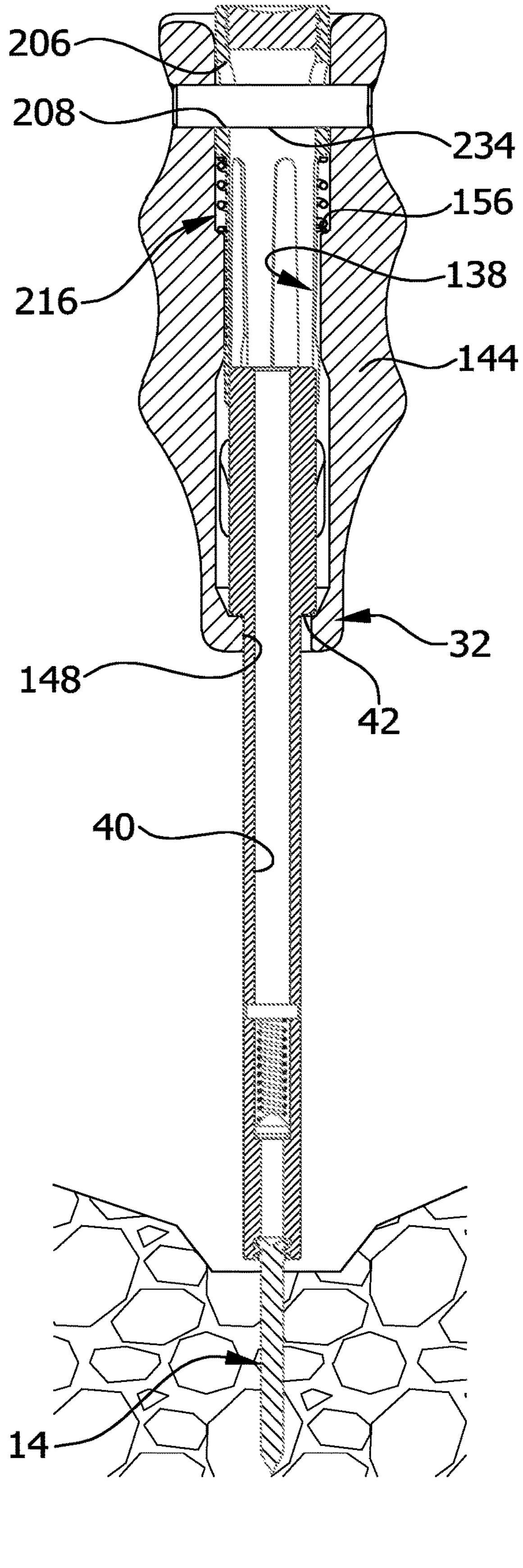
FIG. 12 shows a view similar to FIG. 5, but with the impact body in the proximal stop position in the locking position.

The impact body 26 is configured in the form of a handle 126, which enables an ergonomically shaped outer contour 128 for the handle 126 to be held by one hand 130 of a user. The ergonomic outer contour 128 comprises two annular projections 132 and 134 spaced at a distance from one another, between which an annular groove 136 is formed. On the proximal side of the annular projection 132 and on the distal side of the annular projection 134, an outer diameter of the handle 126 decreases in the proximal and distal direction, respectively. The outer contour 128 is of completely rounded configuration without sharp corners and edges. It is schematically shown in FIGS. 8 to 10 as well as 13 and 14 how the medical impact instrument 12 can be held by a user with one hand.

The impact body 26 has a longitudinal perforation 138 extending coaxially to the shaft longitudinal direction 20. The shaft 18 is accommodated at least partially in the longitudinal perforation 138.

The impact body 26 comprises an annular proximal impact body end face 140 pointing in the proximal direction and a distal impact body end face 142 pointing in the distal direction.

The substantially sleeve-shaped impact body 26 comprises a peripheral wall 144 surrounding the longitudinal axis 28 and a distal delimiting wall 146.

The longitudinal perforation 138 passes through the distal delimiting wall 146. An inner diameter of the longitudinal perforation 138 in the region of the distal delimiting wall 146 corresponds to the outer diameter of the distal shaft portion 36. In this way, a guide face 148 for the distal shaft portion 36 pointing in the direction toward the longitudinal axis is formed in the region of the delimiting wall 146.

On the proximal side of the distal delimiting wall, an inner diameter of the longitudinal perforation 138 initially expands conically and then remains constant on about one third of the total length of the impact body 26. Thus, a recess 150 is formed, which has an inner diameter that is greater both than an outer diameter of the distal shaft portion 36 and greater than an outer diameter of the proximal shaft portion 38. An inner diameter of the recess 150 tapers conically on the proximal side and thus forms a conical clamping face 152. The clamping face 152 delimits the recess 150 in sections with the clamping face 152 pointing in the direction toward the longitudinal axis 28.

The clamping face 152 is adjoined by a hollow-cylindrical portion 154 of the longitudinal perforation 138. An inner diameter of the portion 154 is slightly greater than an outer diameter of the proximal shaft portion 38. The reason for this is explained in the following in more detail.

On the proximal side, an inner diameter of the longitudinal perforation 138 adjoining the portion 154 expands in one step, such that an impact body support face 156 pointing in the proximal direction is formed. The impact body support face 156 is configured in the form of an annular face 158. An inner diameter of the longitudinal perforation 138 commencing from the annular face 158 up to the proximal impact body end face 140 corresponds to about an inner diameter of the recess 150.

Furthermore, a stop element 160 is arranged on the impact body 26. It defines a stop element longitudinal axis 162, which extends transversely, namely perpendicularly in the embodiment depicted in the Figures, to the shaft longitudinal direction 20. The stop element 160 is configured in the form of a stop pin 166 inserted into a transverse bore 164 on the impact body 26.

The transverse bore 164 is formed on the proximal side of the annular face 158, namely closer toward the proximal impact body end face 140 than to the annular face 158. A distance of the stop element 160 from the proximal impact body end face 140, which defines a proximal end 168 of the impact body 26, is thus smaller than a distance of the stop element 160 of the distal impact body end face 142, which defines a distal end 170 of the impact body 26.

Now, in the following, the structure and functioning of the fixing device 34 will be defined in more detail. In the embodiment depicted in the Figures, it comprises a fixing element 172 for being brought into engagement in a force-locking and/or positive-locking manner both with the shaft

18 and with the impact body 26 in one of the arbitrary fixing positions described above between the distal stop position and the proximal stop position.

The fixing element 172 is of sleeve-shaped configuration. An inner diameter of the fixing element 172 is configured corresponding to the outer diameter of the proximal shaft portion 38, such that the fixing element 172 and the proximal shaft portion 38 in the impact position are displaceable in parallel to the shaft longitudinal direction 20. The fixing element 172 is thus also guided on the proximal shaft portion 38.

The fixing element 172 is closed on the proximal side. A closure element 174 is screwed into the fixing element 172 commencing from a proximal end 176 of the fixing element 172. The closure element 174 has a flat depression 178 in order to, for example, partially accommodate a thumb 180 of a user and prevent it from slipping off.

The fixing element 172 comprises a sleeve portion 182. It extends in the distal direction commencing from the proximal end 176. A sleeve-shaped clamping element portion 186 that is reduced in external diameter protrudes from an end face 184 of the sleeve portion pointing in the distal direction, such that part of the end face 184 forms a fixing element support face 188. Said support face 188 is annular and surrounds the clamping element portion 186.

An outer diameter of the clamping element portion 186 expands conically toward its distal end 190 and forms a sliding face 192. The sliding face 192 is adjoined by a cylindrical end portion 194 of the clamping element portion 186. The end portion 194 defines an outer diameter, which is greater than an outer diameter of the clamping element portion 186 on the proximal side of the sliding face 192. The outer diameter of the end portion 194, however, is smaller than an outer diameter of the sleeve portion 182.

The fixing element 172 is configured in the form of a clamping element 196. Formed commencing from the distal end 190 in parallel to the longitudinal axis 28 are a plurality of slits 198, such that a corresponding number of clamping arms 200 are formed. In the embodiment depicted in the Figures, six slits 198 are provided. The slits 198 extend up to the sleeve portion 182. Due to the configuration of the end portion 194, the clamping arms 200 have a thickened portion at their free ends 222. In addition, a remaining portion of the sliding face 192 is formed on each clamping arm 200.

The clamping element portion 186 has an outer diameter, which corresponds to the inner diameter of the portion 154 of the impact body 26. Thus, the fixing element 172 is guided on the impact body 26 in the region of the portion 154 with an outer face of the clamping element portion 186.

Furthermore, a fixing element perforation 202 is formed on the fixing element 172. Said perforation extends transversely, namely perpendicularly in the embodiment depicted in the Figures, to the longitudinal axis 28. The fixing element perforation 202 is formed in the region of the sleeve portion 182 and is formed in the manner of an elongate hole in parallel to the longitudinal axis 28. The stop element 160 passes through the fixing element perforation 202, as can be seen, for example, in FIG. 10. An outer diameter of the stop pin 166 is smaller than a longitudinal extent of the fixing element perforation 202 in parallel to the longitudinal axis 28, such that the fixing element 172 is movable in parallel to the longitudinal axis 28.

The impact body 26 further comprises a fixing element stop device 204. The fixing element stop device 204 comprises a distal fixing element stop 206 and a proximal fixing element stop 208 for delimiting a movement of the fixing element 172 in the distal and proximal direction. In the embodiment depicted in the Figures, the distal fixing element stop 206 is arranged or formed on the fixing element 172 on the proximal side relative to the proximal fixing element stop 208. The distal fixing element stop 206 is formed by an inner end face of the fixing element perforation 202 pointing in the distal direction. The proximal fixing element stop 208 is formed by an inner end face 212 of the fixing element perforation 202 pointing in the proximal direction.

The fixing device 34 further comprises a restoring device 214. It serves the purpose of holding the fixing device 34 in a locking position.

In the locking position the impact body 26 is fixed to the shaft 18 in an arbitrary fixing position. The fixing device 34 is further configured in such a way that it is transferable from the locking position into the impact position, in which the impact body 26 and the shaft 18 are movable relative to one another, and vice versa. In the embodiment depicted in the Figures, the fixing device 34 is configured in such a way that it is able to be brought from the locking position into the impact position against the action of the restoring device 214. Therefore, in the embodiment depicted in the Figures, the fixing element 172 can be moved against the action of the restoring device 214 in order to transfer the fixing device 34 from the locking position into the impact position.

The restoring device 214 comprises a restoring element 216. In the embodiment depicted in the Figures, the restoring element 216 is configured in the form of a spring-elastic element 218. In alternative embodiments, the restoring element is configured in the form of one or more rubber-elastic elements.

In the embodiment depicted in the Figures, restoring element 216 is configured in the form of a compression spring 220.

The restoring element 216 is supported on the fixing element support face 188 of the fixing element 172 on the one hand and on the impact body support face 156 of the impact body 26 on the other hand. The fixing element support face 188 points in the distal direction and, as mentioned, is configured as an annular face. It forms part of the end face 184.

The restoring element 216 is arranged or formed surrounding the fixing element 172. The restoring element 216 surrounds the fixing element 172 in the region of the clamping portion 186. As described, it is supported proximally on the sleeve portion 182, namely the end face 184 thereof.

The fixing element 172 is movable, namely displaceable, for transferring the fixing device 34 from the locking position into the impact position. In the embodiment depicted in the Figures, the fixing element 172 is movable relative to the impact body 26 in the distal direction for transferring the fixing device 34 from the locking position into the impact position.

The functioning of the fixing device 34 is described in the following.

Figure 6:
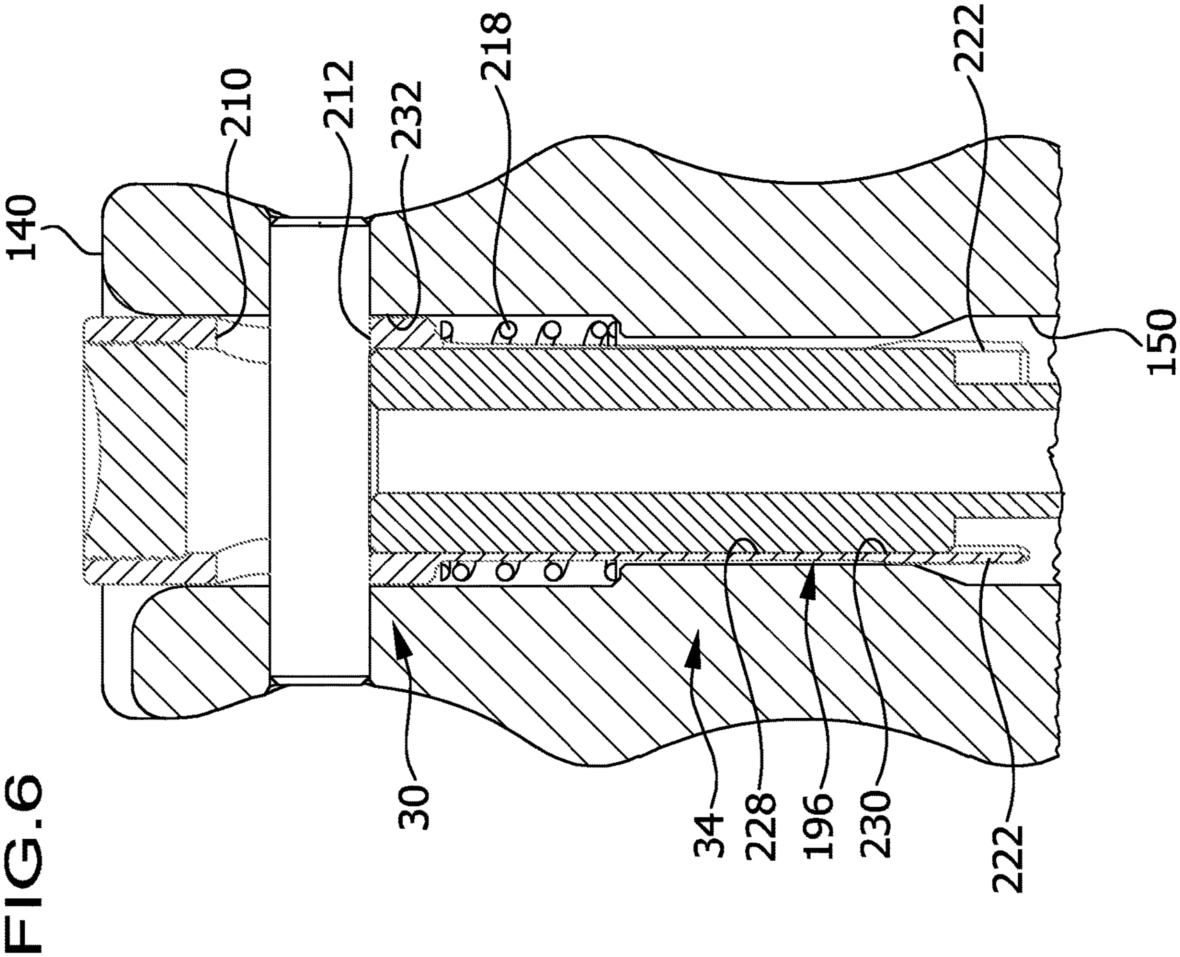
FIG. 6 shows an enlarged view of the region A in FIG. 5.

FIG. 6 shows the locking position. The restoring element 216 pushes the fixing element 172 with the distal end face 212 against the stop element, thereby delimiting a movement of the fixing element 172 in the proximal direction. In this position, the end portions 194 of the clamping arms 200 are drawn back into the region of the portion 154 and interact in a force-locking and/or positive-locking manner both with the shaft 18 and with the impact body 26. The impact body 26 is clampingly held to the shaft 18 in this locking position.

In order to be able to move the impact body 26 relative to the shaft 28, the fixing device 34 must be transferred from the locking position into the impact position. For this purpose, a user can press, for example with their thumb 180, against the closure element 174 on the fixing element 172 and thus move the fixing element 172 in the distal direction against the action of the restoring device 214 until the proximal end face 210 of the fixing element perforation 202 strikes against the stop element 160. During this movement of the fixing element 172 relative to the impact body 26 in the distal direction, the end portions 194 move into the region of the recess 150. Due to the greater inner diameter of the recess 150, it is now possible for the free ends 222 of the clamping arms 200 to be pivotable away from the longitudinal axis 82 of the shaft 18. Or in other words, the clamping arms 200 displaced in the distal direction are no longer biased against the proximal shaft portion 38 by the clamping face 152 or the inner wall face of the portion 154. In the impact position, as it is schematically depicted as an example in FIGS. 8 to 10 as well as 13 and 14, the impact body 26 is displaceable relative to the shaft 18 in parallel to the longitudinal axis 28.

In the locking position, the clamping face 152 or the inner wall face of the portion 154 prevent a movement of the free ends 222 of the clamping arms 200 or the clamping element 196 away from the longitudinal axis 28, such that, as described, the clamping element 196 is held in the direction toward the longitudinal axis 28 in the locking position in order to fix, namely to clamp, the impact body 26 to the shaft 18 in an arbitrary fixing position.

It should also be noted that a first angle of inclination 224 defined between the clamping face 152 and the longitudinal axis 28 is greater than a second angle of inclination 226 defined between the sliding face 192 and the longitudinal axis 28.

Due to the described configuration of the medical impact instrument 12, an inner face 228 of the fixing element 172 pointing in the direction toward the longitudinal axis 28 forms a guide face 230 for the proximal shaft portion 38.

Furthermore, the longitudinal perforation 138 of the impact body 26 from the proximal end thereof forms a guide face 232 pointing in the direction toward the longitudinal axis 28 for the fixing element 172, namely an outer face of the sleeve portion 182.

When the fixing device is transferred from the locking position into the impact position, the impact body 26 can be moved relative to the shaft 18. The proximal shaft portion 38 hereby comprises, as already mentioned, the distal stop 30 with the first stop face 44 acting in the proximal direction.

The impact body 26 comprises a first impact body stop face 234, which cooperates with the first stop face 44 and acts in the distal direction. In the embodiment depicted in the Figures, the stop element 160 defines the first impact body stop face 234. This means that, in the impact position, the impact body 26 is able to be moved only so far in the distal direction until the stop element 160 strikes with the impact body stop face 234 against the first stop face 44, thus against the proximal end face 46 of the shaft 18. Commencing from this extreme position, the impact body 26 is able to be moved in the proximal direction relative to the shaft 18 in the impact position until a second impact body stop face 236 of the impact body 26 strikes against the second stop face 48, thus against the annular face 42, as is schematically depicted as an example in FIG. 13.

The second impact body stop face 236 is also configured in the form of an annular face 238, which points in the proximal direction. It forms a side face of the distal delimiting wall 146. The distal delimiting wall 146 thus comprises the second impact body stop face 236.

A first distance 240 between the first stop face 44 and the second stop face 48 is smaller than a second distance 242 between the first impact body stop face 234 and the second impact body stop face 236. A difference of the distances 240 and 242 determines a maximum movement stroke of the impact body 26 relative to the shaft 18.

In order to also be able to transmit impact pulses with the medical impact instrument 12 to its distal end 24 in the locking position, for example with a hammer, which acts on the proximal impact body end face 140, the proximal end 176 of the fixing element 172 in the locking position does not or substantially does not project beyond the proximal end 168 of the impact body 26. The medical impact instrument 12 can thus also be used in the manner of a chisel. Greater impact pulses can thus optionally be exerted on the distal end 24 than with the impact body 26 when the latter in the impact position is moved with the stop element 160 against the proximal end face 46.

In the case of the medical impact instrument 12 depicted in the Figures, the impact body 26 in the basic position is fixed relative to the shaft 18 and adopts a fixing position. The fixing device 34 hereby adopts the locking position. Using the fixing device 34, the impact body 26 can thus be fixed to the shaft 18 not only in a fixing position between the distal stop position and the proximal stop position, but also in the proximal stop position and in the distal stop position.

For an optimal cleaning of the medical impact instrument 12, a plurality of flush openings 244 and 246 formed on the impact body 26 are provided. The flush openings 244 are formed in the region of the peripheral wall 144 of the impact body 26, the flush openings 246 in the region of the distal delimiting wall 146 of the impact body 26. The flush openings 246 are configured as expansions of the guide face 148, such that only portions thereof remain on which the distal shaft portion 36 is guided when moving the impact body 26 in the impact position relative to the shaft 18.

The flush openings 244 create an access to the longitudinal perforation 138.

The use of the impact instrument 12 is explained briefly in the following in connection with FIGS. 8 to 14.

In order to drive the bone pin 74 coupled, as described above, to the distal end 24 into the bone 76 of the patient, the fixing device 34 is transferred into the impact position by displacing the fixing element 172 in the distal direction as schematically depicted in FIG. 8. Now the impact body 26 can be moved with the stop element 160 against the first stop face 44 in order to transmit an impact pulse to the bone pin 74 and drive same into the bone 76. In the impact position the impact body 26 can be moved back in the proximal direction relative to the shaft 18 and then back again toward the first stop face 44 for transmitting an impact pulse.

The fixing device 34 enables an arbitrary fixing position or an arbitrary clamping of the impact body 26 between the extreme stop positions, namely the distal stop position and the proximal stop position. Such an intermediate position, i.e. a fixing position between the distal stop position and the proximal stop position, is depicted as an example in FIG. 11. Here, the fixing device 34 adopts the locking position. The fixing device 34 is also depicted in the locking position in FIG. 12 as well. However, here the impact body 26 adopts its proximal stop position.

In order to release the bone pin 74 from the bone 76, the fixing device 34 is transferred from the locking position into the impact position and the impact body 26 is moved with the second impact body stop face 236 against the first stop face 48. An impact pulse can thus be exerted with the impact body 26 in the proximal direction on the shaft 18 in order to successively extract the bone pin 74 from the bone 76 by repeatedly exerting such an impact pulse. This is depicted schematically in FIGS. 13 and 14.

The described medical impact instrument 12 enables a simple and uncomplicated coupling thereof with one hand, for example to a medical object 14 anchored in a bone 76. By releasing the fixing element 172 so that the fixing device 34 adopts the locking position, the impact body 26 is able to be immovably secured to the shaft 18 in any one of the described arbitrary fixing positions. A user can now bring the distal end 24 of the impact instrument 12 up to the medical object 14, for example to the head 82 of the bone pin 74, and couple same to the coupling element 64 in the engagement direction 90. This is possible with only one hand, i.e. without the assistance of a second hand, because the distal end 24 in the locking position is fixed relative to the impact body 26, which the user holds and guides with their hand 130.

The described medical system 10 with its medical impact instrument 12 thus enables an improved handling in comparison to known medical impact instruments.

What is claimed is:

1. A medical impact instrument comprising:

a shaft defining a shaft longitudinal direction, a proximal end and a distal end;

an impact body arranged on the shaft and defining a longitudinal axis; and a fixing device, the impact body being moveable in an impact position on the shaft through a range of motion between a distal stop, defining a maximum distal stop position of the impact body relative to the shaft, and a proximal stop, defining a maximum proximal stop position of the impact body relative to the shaft, for transmitting an impact pulse to the distal end of the shaft in a distal direction or a proximal direction, and the fixing device being configured for temporarily fixing the impact body to the shaft in any position within the range of motion between the maximum distal stop position and the maximum proximal stop position.

2. The medical impact instrument according to claim 1, wherein the impact body in a basic position is fixed relative to the shaft.

3. The medical impact instrument according to claim 1, wherein the fixing device is transferable from a locking position, in which the impact body is fixed to the shaft, into the impact position, in which the impact body and the shaft are movable relative to one another, and vice versa.

4. The medical impact instrument according to claim 3, wherein the fixing device comprises a restoring device for automatically holding the fixing device in the locking position.

5. The medical impact instrument according to claim 4, wherein at least one of a) the fixing device is able to be brought from the locking position into the impact position against an action of the restoring device; and b) the restoring device comprises at least one restoring element.

6. The medical impact instrument according to claim 1, wherein the fixing device comprises at least one fixing element for being brought into at least one of force-locking and positive-locking engagement both with the shaft and with the impact body to temporarily fix the impact body to the shaft.

7. The medical impact instrument according to claim 6, wherein the at least one fixing element is configured in the form of a clamping element and comprises at least one clamping arm extending in the longitudinal direction, and wherein a free end of the at least one clamping arm is configured to be movable toward and away from the longitudinal axis.

8. The medical impact instrument according to claim 7, wherein the impact body comprises a recess surrounding the shaft for accommodating the at least one clamping arm.

9. The medical impact instrument according to claim 8, wherein the recess is delimited at least in sections by a clamping face, which points toward the longitudinal axis and which in a locking position cooperates with the at least one clamping arm for preventing a movement of the free end of the at least one clamping arm away from the longitudinal axis or toward the longitudinal axis for clampingly holding the at least one clamping arm.

10. The medical impact instrument according to claim 1, wherein the impact body has a longitudinal perforation extending coaxially to the shaft longitudinal direction and wherein the shaft is accommodated at least partially in the longitudinal perforation.

11. The medical impact instrument according to claim 10, wherein the fixing device comprises at least one fixing element for being brought into at least one of force-locking and positive-locking engagement both with the shaft and with the impact body to temporarily fix the impact body to the shaft, and wherein the longitudinal perforation of the impact body forms a guide face pointing toward the longitudinal axis for the at least one fixing element.

12. The medical impact instrument according to claim 11, wherein a proximal shaft portion of the shaft comprises a first stop face that acts in a proximal direction, and wherein the impact body comprises a first impact body stop face that acts in a distal direction, wherein the first stop face and the first impact body stop face interact to define the maximum distal stop position.

13. The medical impact instrument according to claim 12, wherein the impact body comprises a stop element, which defines the first impact body stop face.

14. The medical impact instrument according to claim 1, wherein the impact body comprises at least one flush opening.

15. The medical impact instrument according to claim 1, wherein the medical impact instrument comprises a coupling device for temporarily coupling to a medical object.

16. The medical impact instrument according to claim 15, wherein the coupling device comprises a first coupling element, which is configured to be brought into at least one of force-locking and positive-locking engagement with a corresponding second coupling element comprised by the medical object in a coupling position.

17. The medical impact instrument according to claim 15, wherein the coupling device comprises a securing device for securing a medical object to the medical impact instrument in a coupling position in a force-locking and/or positive-locking manner.

18. The medical impact instrument according to claim 17, wherein the securing device is able to be brought from a release position, in which the medical impact instrument and the medical object are able to be brought into engagement in an engagement direction, into a securing position, in which a movement of the medical impact instrument and the medical object relative to one another in or opposite to the engagement direction is blocked.

19. The medical impact instrument according to claim 18, wherein the securing device comprises a biasing device for automatically transferring the securing device from the release position into the securing position.

20. The medical impact instrument according to claim 19, wherein the biasing device at least one of:

a) is configured to hold the securing device in the securing position under bias and b) comprises at least one biasing element.

21. A medical impact instrument comprising:

a shaft defining a shaft longitudinal direction, a proximal end and a distal end;

an impact body arranged on the shaft and defining a longitudinal axis; and a fixing device, the impact body being moveable in an impact position on the shaft between a distal stop, defining a distal stop position of the impact body, and a proximal stop, defining a proximal stop position of the impact body, for transmitting an impact pulse to the distal end of the shaft in a distal direction or a proximal direction, and the fixing device being configured for temporarily fixing the impact body to the shaft in at least one fixing position between the distal stop position and the proximal stop position, wherein the fixing device comprises at least one fixing element for being brought into at least one of force-locking and positive-locking engagement both with the shaft and with the impact body in the at least one fixing position, and wherein the at least one fixing element is configured in the form of a clamping element and comprises at least one clamping arm extending in the longitudinal direction and having a free end pointing in the distal direction, and wherein the free end of the at least one clamping arm is configured to be movable toward and away from the longitudinal axis.

22. A medical impact instrument comprising:

a shaft defining a shaft longitudinal direction, a proximal end and a distal end;

an impact body arranged on the shaft and defining a longitudinal axis; and a fixing device, the impact body being moveable in an impact position on the shaft between a distal stop, defining a distal stop position of the impact body, and a proximal stop, defining a proximal stop position of the impact body, for transmitting an impact pulse to the distal end of the shaft in a distal direction or a proximal direction, and the fixing device being configured for temporarily fixing the impact body to the shaft in at least one fixing position between the distal stop position and the proximal stop position, wherein the shaft comprises a distal stop face configured to interact with the distal stop to limit a movement of the impact body relative to the shaft in the distal direction, and a proximal stop face configured to interact with the proximal stop to limit a movement of the impact body relative to the shaft in the proximal direction, wherein a distance between the distal stop face and the proximal stop face is fixed.

* * * * *